United States Patent
Küçük

(10) Patent No.: US 12,318,587 B2
(45) Date of Patent: Jun. 3, 2025

(54) SYRINGE BODY

(71) Applicant: SCHOTT PHARMA SCHWEIZ AG, St. Gallen (CH)

(72) Inventor: Mustafa Küçük, Staad (CH)

(73) Assignee: SCHOTT PHARMA SCHWEIZ AG, St. Gallen (CH)

( * ) Notice: Subject to any disclaimer, the term of this patent is extended or adjusted under 35 U.S.C. 154(b) by 486 days.

(21) Appl. No.: 16/599,548

(22) Filed: Oct. 11, 2019

(65) Prior Publication Data
US 2020/0114084 A1    Apr. 16, 2020

(30) Foreign Application Priority Data
Oct. 11, 2018  (DE) .................... 20 2018 105 835.5

(51) Int. Cl.
*A61M 5/31* (2006.01)
*A61M 5/315* (2006.01)

(52) U.S. Cl.
CPC .......... *A61M 5/3137* (2013.01); *A61M 5/315* (2013.01)

(58) Field of Classification Search
CPC ........ A61M 5/28; A61M 5/31; A61M 5/3135; A61M 2005/3139; A61M 5/3137; A61M 5/315; A61M 5/3129; A61M 5/31513
See application file for complete search history.

(56) References Cited

U.S. PATENT DOCUMENTS

| | | | | |
|---|---|---|---|---|
| 2,551,339 A | * | 5/1951 | Ryan | A61M 5/28 604/232 |
| 2,834,346 A | * | 5/1958 | Adams | A61M 5/28 604/242 |
| 4,994,012 A | * | 2/1991 | Nakayama | A61B 6/107 600/431 |
| 5,788,670 A | | 8/1998 | Reinhard | |
| 6,004,299 A | | 12/1999 | Arai | |
| 2002/0052577 A1 | * | 5/2002 | Shimazaki | A61M 5/3129 604/192 |
| 2004/0013853 A1 | * | 1/2004 | Mandzsu | B32B 27/32 428/143 |
| 2004/0034323 A1 | | 2/2004 | Manthey | |
| 2009/0137966 A1 | | 5/2009 | Rueckert | |
| 2009/0171297 A1 | | 7/2009 | Smith | |
| 2012/0041388 A1 | | 2/2012 | Blomquist | |

(Continued)

FOREIGN PATENT DOCUMENTS

| | | | |
|---|---|---|---|
| CA | 2009942 A1 | * | 8/1990 |
| CA | 2005608 | | 3/1994 |

(Continued)

*Primary Examiner* — James D Ponton
*Assistant Examiner* — Hong-Van N Trinh
(74) *Attorney, Agent, or Firm* — Ruggiero McAllister & McMahon LLC

(57) ABSTRACT

A syringe body for a pharmaceutical syringe is provided. The syringe includes cylindrical cavity, a finger flange, and an anti-slip element. The cylindrical cavity has a first end face with a cone and a second, open end face configured to receive a piston. The finger flange is arranged around a circumference of the second, open end face. The finger flange has a first surface that faces the cone. The anti-slip element is a roughened area on the first surface. The roughened area exhibits an arithmetic mean roughness value between 0.8 μm and 150 μm.

14 Claims, 2 Drawing Sheets

(56) References Cited

U.S. PATENT DOCUMENTS

| | | | |
|---|---|---|---|
| 2013/0178737 A1* | 7/2013 | Anelli | A61M 5/007 |
| | | | 600/432 |
| 2016/0051774 A1 | 2/2016 | Sugiki | |
| 2016/0129193 A1 | 5/2016 | Komann | |

FOREIGN PATENT DOCUMENTS

| | | |
|---|---|---|
| CA | 2908822 | 5/2019 |
| CN | 101439211 | 5/2009 |
| CN | 105263544 | 1/2016 |
| DE | 4445969 | 3/1996 |
| JP | H10137336 | 5/1998 |
| JP | 2001187140 | 7/2001 |
| KR | 101841557 | 3/2018 |
| WO | 2014178242 | 11/2014 |

* cited by examiner

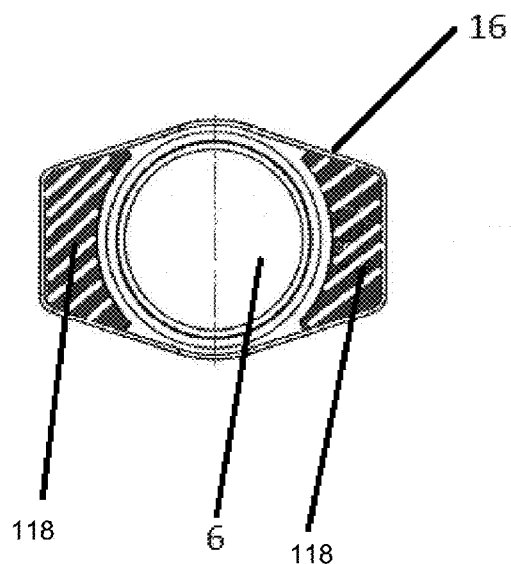
FIG. 3
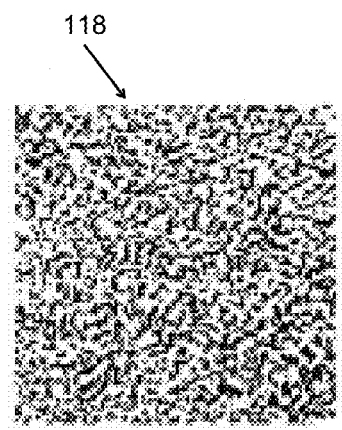 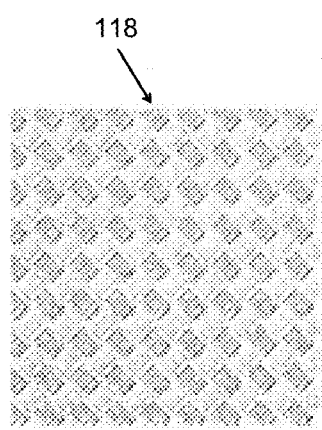
FIG. 4  FIG. 5

SYRINGE BODY

CROSS REFERENCE TO RELATED APPLICATIONS

This application claims benefit under 35 USC X119 of German Application 20 2018 105 835.5 filed Oct. 11, 2018, the entire contents of which are incorporated herein by reference.

BACKGROUND

1. Field of the Invention

The invention relates to a syringe body for a pharmaceutical or cosmetic syringe, comprising a cylindrical cavity that has a first end face with a cone, a second, open end face for inserting a piston, and a finger flange arranged around the circumference of the open end face, wherein the finger flange has an anti-slip element on the surface facing the cone, for preventing a finger from slipping off during the injection process and a method for applying or administering a pharmaceutical or a cosmetic.

2. Description of Related Art

Syringe refers to a medical instrument that is used for administering (injecting) liquid or fluid medications or cosmetics—known as injectables, which are generally also referred to as fluids for abbreviating, within the scope of the present disclosure. A syringe typically comprises a syringe body with a cylindrical cavity and a piston moved therein. Typically, a cone is provided on one end face of the cylinder, optionally with a screw thread, for connecting a cannula or a hose thereto. On the opposite side, i.e. on the other end face of the cylinder, the latter is open, so that the piston is introduced on this side, which piston can be used for loading the syringe, i.e. for sucking in a fluid pharmaceutical or cosmetics through the cone by pulling out the piston, as well as for administering the pharmaceutical or the cosmetics.

Alternatively, the syringe may already be filled with a pharmaceutical or a cosmetic, by the producer, in particular be filled sterilely so that filling with the pharmaceutical or the cosmetic before its application is not needed.

Furthermore, the presently disclosed syringe bodies and syringes comprising these bodies may be used in the area of human medicine as well as in the area of veterinary medicine.

For administering the fluid pharmaceutical or cosmetic from the cylindrical hollow body, the piston is pressed in, so that the contents are pressed through the cone. In order to allow this operation to be performed with one hand, a finger flange is usually provided circumferentially around the open end face, i.e. around the opening into which the piston is introduced. This finger flange provides a gripping option for holding the syringe body against the pressure applied on the piston. Usually, the syringe body is held with the index and middle fingers on the finger flange, and the thumb is used to press the piston into the syringe body.

In order to prevent a finger from slipping off during the injection process, especially larger syringes of more than about 20 ml often have an anti-slip element arranged on the finger rest, i.e. on the surface of the finger flange facing the cone. Often, raised transverse webs are provided for this purpose, which are aligned spaced apart tangentially.

The document U.S. Pat. No. 4,994,012 B shows a corresponding syringe body having tungsten for radiation shielding, and a syringe having that body.

In U.S. Pat. No. 6,004,299 B, a syringe with a syringe body consisting of glass is disclosed which defines lateral finger bearing surfaces which seem to form longitudinal ribs.

US 2012/0041388 A shows a gripping device for a syringe body which device may almost completely be enclosed with the finger of one hand, except the thumb. Due to the size of the gripping device, inherent to its functional principle, in to which the syringe body has to be inserted, the particular syringe body, however, gets less manageable, because the sensitive movement of the particular fingers operating the syringe is not more available, but only movements of the whole hand. Furthermore, it seems to be cumbersome to mount the gripping device at the syringe body, first, in order to be able to use the syringe afterwards.

Also the document US 2013/0178737 A shows a gripping device for a syringe body, with which device it seems to be cumbersome to mount the gripping device at the syringe body first, in order to be able to use the syringe afterwards.

SUMMARY

It has been found that for example designs having longitudinal ribs may lead to problems when the syringe bodies are put down: syringe bodies cast according to the above-described principle tend to tilt when placed with the flange surface on a flat support surface.

It is therefore an object of the invention to provide a syringe body of the generic type mentioned above, which stands particularly stably.

This object is achieved by the invention by providing the anti-slip element with a surface that exhibits an arithmetic mean roughness value between 0.8 µm and 150 µm.

The invention is based on the consideration that a particularly stable stand would be achieved by avoiding tilting of the syringe body when being placed on the flange. It was found that the tilting is caused due to an irregular surface which evidently arises during the casting of the flange. In particular, it was recognized that sink marks arise as a kind of sagging, with an extent corresponding to that of the transverse webs described above. Accordingly, raised features for enhancing the grip lead to sink marks on the opposite side and thus to an irregular surface. Based on the further finding that such sink marks are caused by local accumulation of material due to the shape of the transverse webs, such material accumulation should be avoided. However, in order to still retain the grip and anti-slip behavior, an alternative design should be provided which does not lead to local material accumulations of the anti-slip element. For this purpose, a uniformly roughened surface should be used, which avoids local accumulations of material. However, in order to guarantee the grip, an appropriate degree of roughness of the surface should be ensured. It was found in experiments that a mean roughness value of more than 0. µm is suitable to ensure the desired slip resistance.

Preferably, the anti-slip element is provided in the form of a surface exhibiting an arithmetic mean roughness value between 5 µm and 100 µm, even more preferably between 10 µm and 50 µm.

In an advantageous embodiment, the finger flange defines a plane together with the open end face, i.e. the opening for introducing the piston of the syringe lies in the plane of the flat finger flange. As described above, the problem of tilting is precisely an issue with such syringe bodies when being placed on the plane of the flange, so that the above-described embodiment of the anti-slip element offers particular advantages.

Furthermore, the flange advantageously has a mirror-symmetrical shape with respect to a surface containing the axis of the cylindrical cavity. Thus, such a flange has two symmetrical extensions on both sides of the opening for the piston, so that a suitable contact surface is provided for the index and middle fingers. Accordingly, an anti-slip element is provided on both contact surfaces.

In a further advantageous embodiment, a labeling surface is provided on the surface of the finger flange facing away from the cone. In such an embodiment, the above-described embodiment of the anti-slip element offers additional advantages: Usually, the syringe body is made of a transparent material. Therefore, the anti-slip element shines through on the rear face of the labeling surface. The transverse webs described above impair the readability of the labeling surface due to refraction and reflection effects. By contrast, a rough surface as described above significantly improves the readability of the labeling.

According to yet another advantageous embodiment, the anti-slip element covers more than 60%, preferably more than 80% of the surface of the finger flange. As a result, a sufficient or particularly good slip resistance is ensured.

Moreover, the surface advantageously has a regular geometric texture, i.e. a repetitive pattern, or an irregular random texture, i.e. a random distribution of raised and recessed points.

Furthermore, the anti-slip element is advantageously spaced apart from the lateral surface of the cylindrical cavity. In other words: the rough surface of the anti-slip element does not extend to the cylindrical portion of the syringe body but ends shortly (e.g. more than 1 mm) in front thereof and merges into a smooth surface that then extends to and adjoins the cylindrical portion. This ensures that the nest has contact to the smooth surface in the casting process, so that particle formation is avoided.

Advantageously, the syringe body, i.e. the wall surrounding the cavity, the cone, and the finger flange are integrally formed, i.e. they are produced directly by injection molding, for example. Especially in the case of such syringe bodies produced by injection molding, the issue of sink marks as mentioned in the introductory part becomes particularly apparent. On the other hand, in the case of glass syringes it may be advantageous to use attachable separate finger flanges which are fitted around the wall, since non-cylindrically symmetrical finger flanges made of glass are difficult to produce.

In an advantageous embodiment, the syringe body is made of a plastic material, in particular a cyclic olefin polymer or copolymer. In particular such syringe bodies are advantageously formed integrally, i.e. in one piece.

A pharmaceutical syringe advantageously comprises a syringe body as described above and a movable piston that is disposed in the cylindrical cavity.

The advantages achieved by the invention in particular include that by using a rough surface with an arithmetic mean roughness value of more than 0.8 µm as an anti-slip element on the finger flange of a syringe, a particularly good grip is achieved on the one hand, and on the other a particularly smooth surface of the flange on the opposite side, so that tilting is avoided when placed upright. Moreover, such a surface improves the readability of an optionally provided labeling.

In laboratory medical or clinical daily routine, when preparing and applying corresponding preparations, in particular when injecting them, substances are used which have a high risk of contamination for the particular user and also for the patient.

These may for example be delivering ionizing radiation or biologically active substances of the preparation to be applied, which hold a high damage risk, also for the health personnel, in particular at the time when for example a syringe body is not handled properly what may for example happen, when the syringe body is not exactly positioned during its handling, or the syringe body requires an increased effort, for example when applying highly viscous fluids.

If slipping off the syringe body takes place, when handling the syringe in these cases, such a substance may exit and get in contact with the patient as well as with the health personnel. In an undesirable manner.

But also a less correctly positioned injection may then be harmful for the particular patient, if, for example in case of an intramuscular depot delivery, a vessel such as a sanguiferous or a lymph-transporting vessel is supplied with the substance to be delivered.

Normally, this situation is additionally complicated, if for example protective gloves are worn during the handling mentioned before.

Here, the presently disclosed syringe with its syringe body proves to be extremely helpful, because, due to the presently disclosed anti-slip element with its surface formed with an arithmetic mid surface parameter between 0.8 µm and 150 µm this handling, is clearly improved.

On the one hand, the probability of slipping off is highly reduced and, on the other hand, the more exact handling, for example when positioning the injection to be done, is considerably improved.

These advantages in particular appear when using the presently disclosed syringe with its syringe body in a medical or a cosmetic method, comprising injecting or administering a medical preparation in oral surgery, in particular injecting an anesthetic in the inside of the mouth of a patient, and/or injecting or administering a medical preparation in ophthalmology, in particular for suppressing lid's blinking reflexes or for widening the pupil of a patient, and/or injecting or administering a medical preparation in nephrology, in particular for administering marker substances for tracing fluid dynamic processes, and/or injecting or administering a medical preparation in nuclear medicine for administering radioactively emitting isotopes, preferably for tumor treatment, and/or injecting or administering a cosmetic preparation, such as hyaluronic acid or a botox-based preparation.

These advantages are even more distinct, if a fluid for example is injected or administered, which is administered with protective gloves, in particular with protective gloves for one-off use according to DIN EN 455 "Medical gloves for one-off use".

Here, a fluid, for example, may be injected or administered, which comprises a patient-individualized preparation containing a genetically modified substance, and/or comprises a biologically or microbiologically produced or augmented preparation, and/or comprises a patient-individualized, tumor-specific marker substance.

A further advantageous use of the syringe with its syringe body is existent with a method with which a fluid is injected or administered which is administered with protective gloves, in particular with protective gloves against ionizing radiation and radioactive contamination, in particular with protective gloves according to DIN EN 421.

Here for example, a fluid may be injected or administered with clearly increased security which fluid generates ionizing radiation, which fluid in particular comprises a radioactive, patient-individualized tumor marker substance and/or a preparation containing radioactive, patient-individualized gene sequences.

Although commercial aspects are not given priority with the sought improvements, it shall be noted for the sake of completeness, that the before-mentioned preparations, in particular patient-individualized preparations may cause very considerable costs, when producing them, which costs particularly occur, if an incorrectly made application leads to an at least partial loss of the preparation.

Also the frequency and likelihood of such cases may be reduced with the herein disclosed method.

DESCRIPTION OF THE DRAWINGS

Exemplary embodiments of the invention will be explained in more detail with reference to the drawings, wherein:

FIG. 3 illustrates an improved anti-slip element; and

FIGS. 4 and 5 show views of different rough surfaces.

In all drawings, similar parts are designated by the same reference numerals.

DETAILED DESCRIPTION

Figure 1:
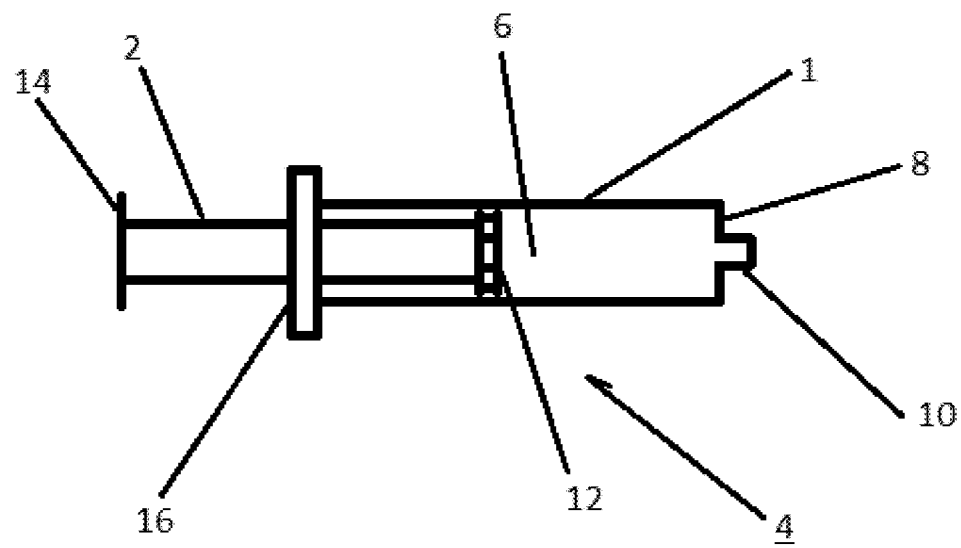
FIG. 1 is a schematic view of a pharmaceutical syringe.

FIG. 1 shows a schematic view of a syringe body 1 with a piston 2, which together define a pharmaceutical syringe 4. The syringe body 1 is made of a transparent plastic material, in exemplary embodiments of a cyclic olefin polymer or copolymer. It has a cavity 6 with a circular cylindrical wall. The latter is essentially closed at a first end face 8, however, the liquid contained in the cavity 6 can be pushed out there through a cone 10. This is done by pressing the piston 2 into the cavity so that the piston head 12 which is circular and engages on the wall of the cavity 6 exerts a pressure onto the liquid.

For introducing the piston 2 into the cavity 6, the latter is open on the second end face of the cylinder. For pressing in the piston 2, the latter has a pressure surface 14 on the side opposite to the piston head 12, which is typically operated by the thumb of the user. For exerting a counter-pressure, a collar-shaped finger flange 16 is integrally molded around the circular opening of the cavity 6 by casting so as to form a flat surface around the opening with a surface normal defined by the axis of the cylindrical cavity 6.

In the exemplary embodiment, the wall of the cavity 6, the cone 10, and the finger flange 16 are made in one piece. Since the syringe body 1 is made of a plastic material in the present exemplary embodiment, the syringe body 1 may be produced by injection molding, for example. In an alternative embodiment, however, the wall and the cone 10 may be made of glass. In this case, the finger flange 16 is provided in the form of a separate attachable part.

Figure 2:
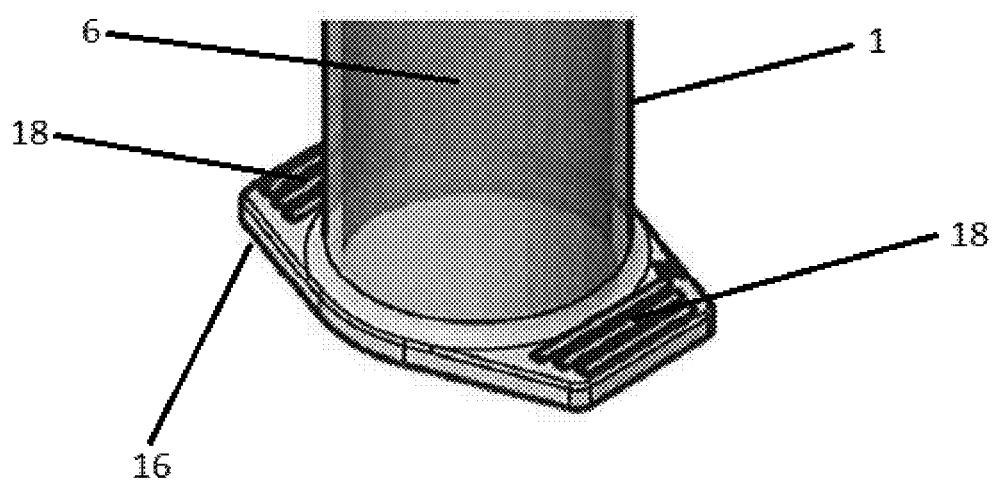
FIG. 2 shows an anti-slip element on the finger flange of the syringe in a three-dimensional view.

The design of the finger flange 16 will be described in more detail below. FIG. 2 shows a three-dimensional partially cutaway view of a syringe body 1 according to the prior art in the region of the finger flange 16. The finger flange 16 has a mirror-symmetrical shape with respect to a plane through the axis of the cylindrical cavity 6, and has a trapezoidal outer contour on each of the symmetrical sides, with a long base of the trapezoidal shape being only slightly larger than the outer diameter of the cylinder.

As a result, two wings of the finger flange 16 are defined, one of which can be gripped by the user's index finger, the other by the middle finger, while the thumb presses down the piston 2 as described above. In order to prevent slippage of the index and middle fingers 16, anti-slip elements 18 are provided on the surface of each of the wings of the finger flange facing the cone 10. In the state of the art according to FIG. 2, these anti-slip elements 18 are formed as three clearly raised transverse webs which extend parallel to the base of the trapezoid of the wing.

Here, the problem arises that in the position shown in FIG. 2, namely when the syringe body 1 stands on the finger flange 16, it is not stable, but tends to tilt. This is caused by sagging on the side opposite to the transverse webs of the finger flange. In addition, the transverse webs impair the reading of a labeling arranged on the opposite side of the finger flange 16.

In order to solve these problems, the anti-slip elements of the present application are formed as a roughened area 118 as shown in FIG. 3, which will be described merely by referring to the differences thereof compared to FIG. 2. FIG. 3 shows the finger flange 16 in the plan view. Here, the transverse webs of anti-slip elements 18 have been eliminated. Instead, finger flange 16 has roughened area 118 that defines the anti-slip element.

Roughened area 118 is roughened in the hatched area and accounts for more than 80% of an area of the finger flange 16. In the preferred exemplary embodiment, roughened area 118 has an arithmetic mean roughness value between 10 and 50 μm. For determining this measured value, roughened 118 is scanned along a defined measuring path and all height and depth differences of the rough surface are recorded. After calculating the definite integral of this roughness curve along the measuring path, the result thereof is finally divided by the length of the measuring path in order to obtain the arithmetic mean roughness value.

The roughened area 118 is created by appropriate design of the casting mold. FIGS. 4 and 5 shows exemplary options of designing the roughened area 118 of FIG. 3. FIG. 4 shows a chaotic or irregular random texture or roughening at area 118, while FIG. 5 shows a regular geometric texture or pattern roughening at area 118.

Moreover, it can be seen in FIG. 3, that the hatched end face of the area 118 is formed in this way does not reach the outside diameter of the cavity 6, rather, a smooth transition area remains between the surface 118 and the lateral surface of the cavity 6.

LIST OF REFERENCE NUMERALS

1 Syringe body
2 Piston
4 Syringe
6 Cavity
8 End face
10 Cone
12 Piston head
14 Pressure surface
16 Finger flange
18 Anti-slip element as transverse webs
118 Anti-slip element as a roughened area

What is claimed is:

1. A syringe body for a pharmaceutical syringe, comprising:
   a cylindrical cavity having a first end face with a cone and a second, open end face configured to receive a piston;
   a finger flange arranged around a circumference of the second, open end face, the finger flange having a first surface that faces the cone and a second surface opposite the first surface; and
   an anti-slip element defined as a roughened area on the first surface that comprises an irregular random texture having a random distribution of raised and recessed points that is created by a design of a casting mold, the roughened area exhibiting an arithmetic mean roughness value between 10 µm and 50 µm, and wherein the roughened area does not extend to the cylindrical cavity but ends more than 1 mm in front thereof and merges into a smooth surface that then extends to and adjoins the cylindrical cavity,
   wherein the cylindrical cavity, finger flange, and anti-slip element are injection molded as one piece with the roughened area avoiding local accumulations of material in the finger flange so that the second surface defines a flat plane together with the second, open end face and so that the syringe body is configured to stably stand on the second surface.

2. The syringe body of claim 1, wherein the finger flange has a mirror-symmetrical shape with respect to a surface containing an axis of the cylindrical cavity.

3. The syringe body of claim 1, wherein the second surface faces away from the cone.

4. The syringe body of claim 3, wherein the second surface is configured to receive a label.

5. The syringe body of claim 4, wherein at least the finger flange is made of a transparent material such that the roughened area shines through on the second surface to improve readability of the label.

6. The syringe body of claim 1, wherein the roughened area covers more than 60% of a surface area of the finger flange.

7. The syringe body of claim 1, wherein the roughened area covers more than 80% of a surface area of the finger flange.

8. The syringe body of claim 1, wherein the cylindrical cavity, finger flange, and anti-slip element consist of a plastic material.

9. The syringe body of claim 8, wherein the plastic material comprises cyclic olefin polymer or copolymer.

10. A pharmaceutical or cosmetic syringe, comprising the syringe body of claim 1 and the piston movably disposed in the cylindrical cavity.

11. The syringe of claim 10, further comprising a fluid in the cylindrical cavity, the fluid being selected from a group consisting of a medical preparation, a cosmetic preparation, a patient-individualized preparation containing a genetically modified substance, a patient-individualized preparation containing a biologically or microbiologically produced or augmented preparation, and a patient-individualized, tumor-specific marker substance.

12. The syringe of claim 10, further comprising a fluid in the cylindrical cavity, the fluid being selected from a group consisting of an ionizing radiation generating fluid, a radioactive, patient-individualized tumor marker substance, a preparation containing radioactive, patient-individualized gene sequences, and combinations thereof.

13. A syringe body for a pharmaceutical syringe, comprising:
   a cylindrical cavity having a first end face with a cone and a second, open end face configured to receive a piston;
   a finger flange arranged around a circumference of the second, open end face, the finger flange having a first surface that faces the cone and a second surface opposite the first surface, the second surface is configured to receive a label; and
   a roughened area on the first surface that comprises an irregular random texture having a random distribution of raised and recessed points that is created by a design of a casting mold, the roughened area exhibiting an arithmetic mean roughness value between 10 µm and 50 µm, the roughened area does not extend to the cylindrical cavity but ends more than 1 mm in front thereof and merges into a smooth surface that then extends to and adjoins the cylindrical cavity,
   wherein the cylindrical cavity, finger flange, and roughened area are injection molded from a transparent material as one piece with the roughened area positioned with respect to a location that receives the label to shine through the transparent material to improve readability of the label when viewed from the second surface when the second surface receives the label.

14. A syringe body for a pharmaceutical syringe, comprising:
   a cylindrical cavity having a first end face with a cone and a second, open end face configured to receive a piston;
   a finger flange arranged around a circumference of the second, open end face, the finger flange having a first surface that faces the cone and a second surface opposite the first surface, the second surface is configured to receive a label; and
   a roughened area on the first surface that comprises an irregular random texture having a random distribution of raised and recessed points that is created by a design of a casting mold, the roughened area exhibiting an arithmetic mean roughness value between 10 µm and 50 µm, the roughened area does not extend to the cylindrical cavity but ends more than 1 mm in front thereof and merges into a smooth surface that then extends to and adjoins the cylindrical cavity,
   wherein the cylindrical cavity, finger flange, and roughened area are injection molded from a transparent material as one piece with the roughened area avoiding local accumulations of material in the finger flange such that the second surface defines a flat plane together with the second, open end face so that the syringe body is configured to stably stand on the second surface, and
   wherein the roughened area is positioned with respect to a location that receives the label so that the roughened area shines through the transparent material to improve readability of the label when viewed from the second surface when the second surface receives the label.

* * * * *